United States Patent [19]

Baildon

[11] Patent Number: 4,919,126
[45] Date of Patent: Apr. 24, 1990

[54] FLEXIBLE ORAL AIRWAYS AND METHODS

[76] Inventor: David E. Baildon, Callahan Rd., P.O. Box 2647, Lake City, Fla. 32056-2647

[21] Appl. No.: 47,324

[22] Filed: May 8, 1987

[51] Int. Cl.⁵ ............................................. A61M 16/00
[52] U.S. Cl. ............................ 128/207.14; 128/200.26
[58] Field of Search ....................... 128/200.26, 207.14, 128/207.15, 207.16, 207.17

[56] References Cited

U.S. PATENT DOCUMENTS

| 2,537,674 | 1/1951 | Johnson | 128/207.14 |
| 2,599,521 | 6/1952 | Berman | 128/207.14 |
| 2,705,959 | 4/1955 | Elmore | 128/207.14 |
| 3,419,004 | 12/1968 | Berman | 128/207.14 |
| 3,754,554 | 8/1973 | Felbarg | 128/207.14 |
| 3,930,507 | 1/1976 | Berman | 128/207.14 |
| 4,338,930 | 7/1982 | Williams | 128/207.14 X |
| 4,363,320 | 12/1982 | Kossove | 128/207.14 |
| 4,498,473 | 2/1985 | Gereg | 128/207.15 |

Primary Examiner—Gerald A. Michalsky

[57] ABSTRACT

Disclosed are artificial airways dimensioned for extension through the oral airway of a medical patient during treatment, the artificial airway having a longitudinal air passageway and being sufficiently pliable so as to conform to the specific configuration of a particular patient during insertion, and having rigid regions which maintain the specific patient configuration after insertion and avoid bending in certain directions.

45 Claims, 5 Drawing Sheets

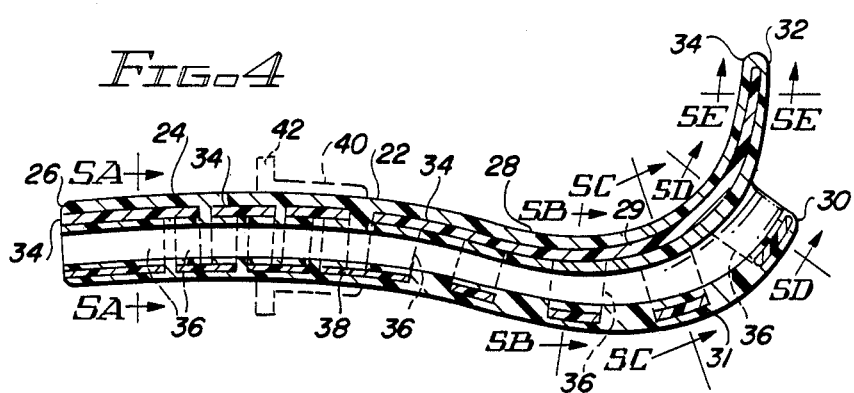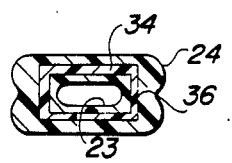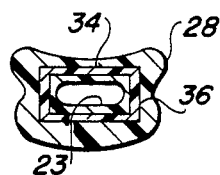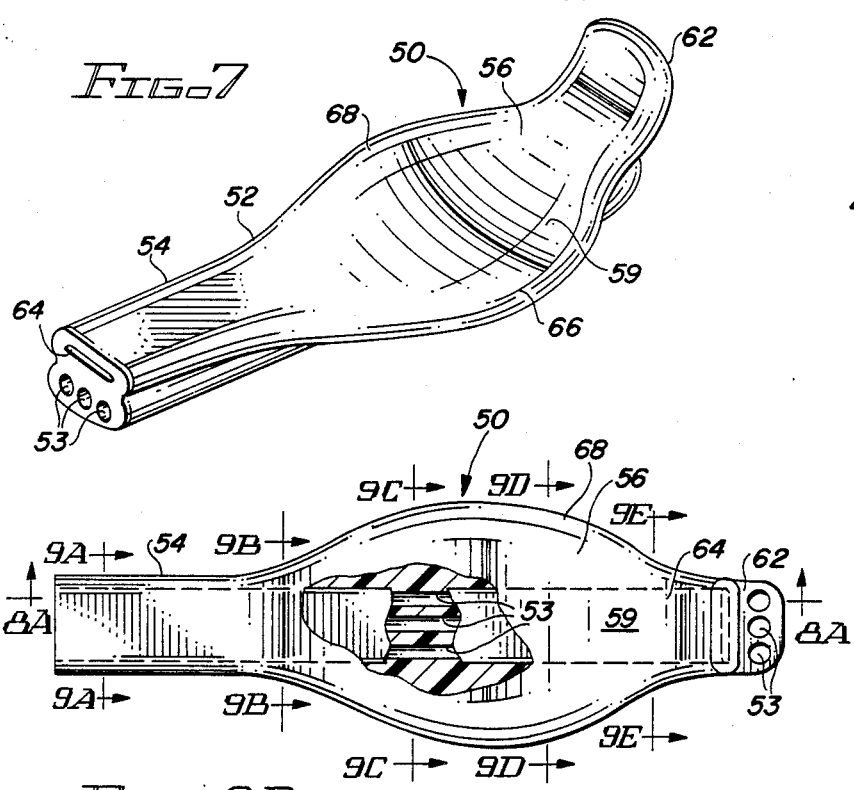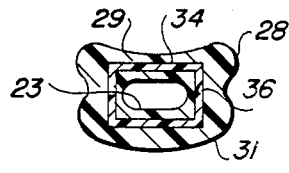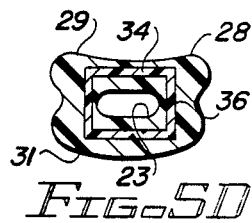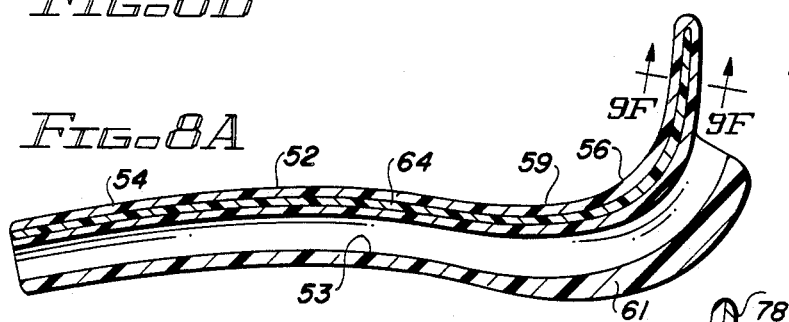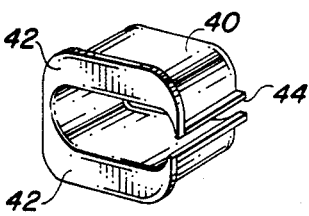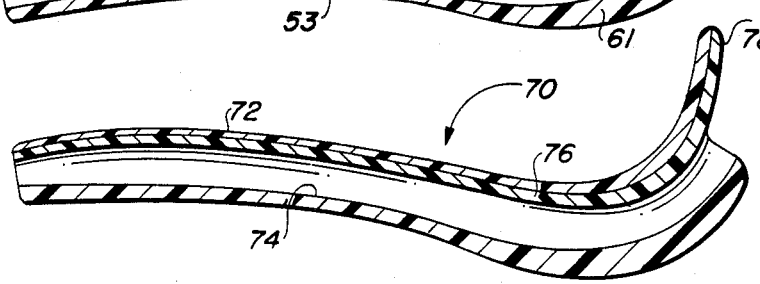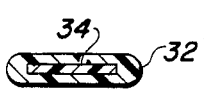

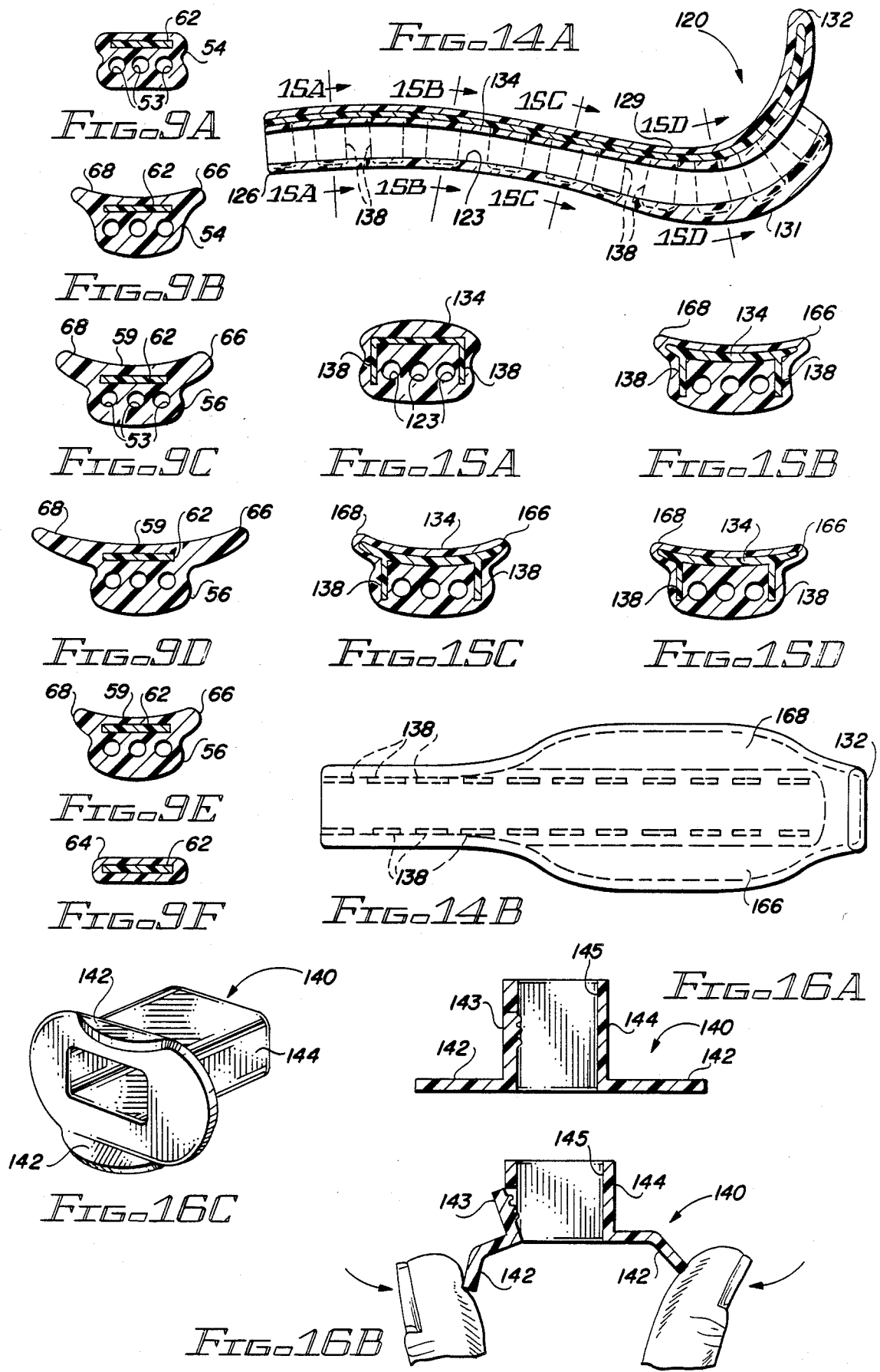

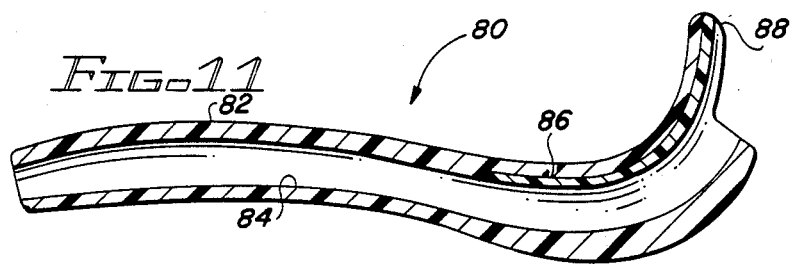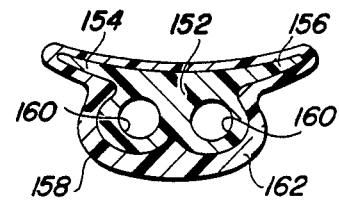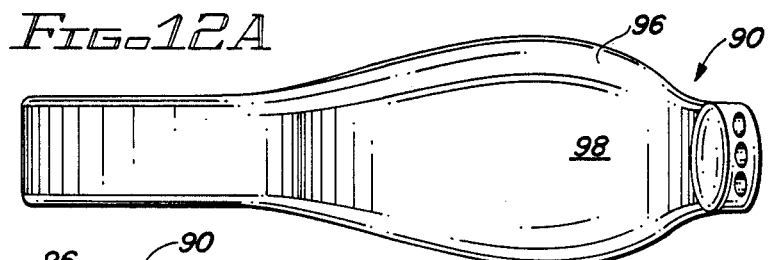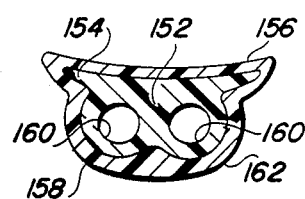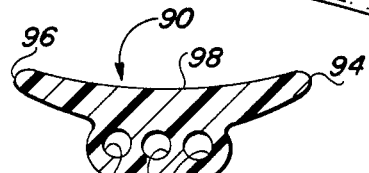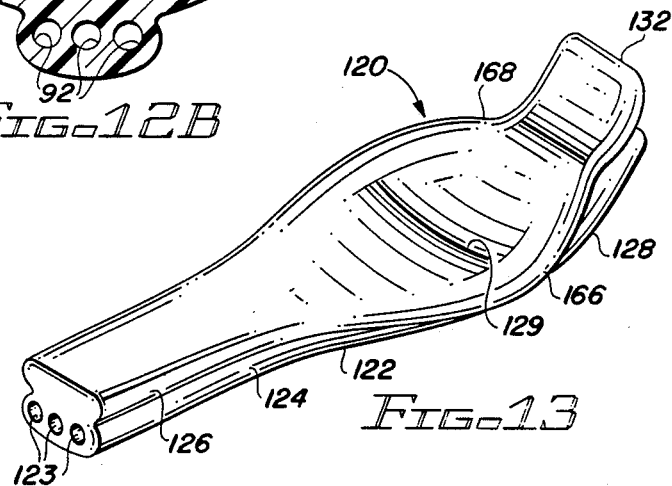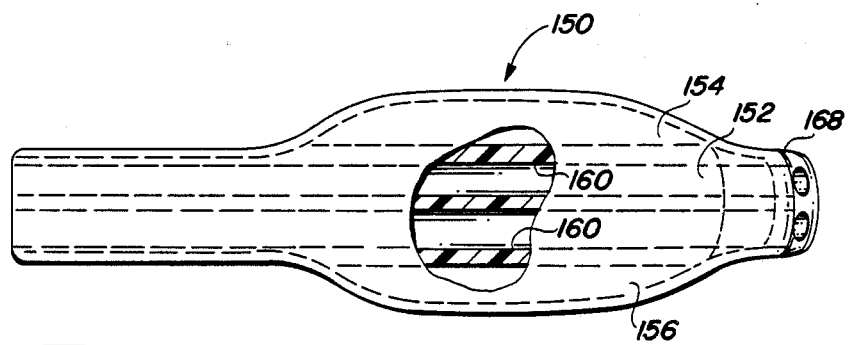

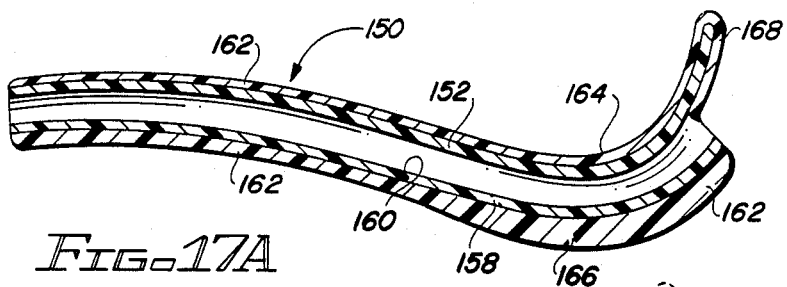
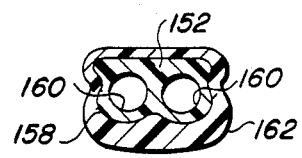
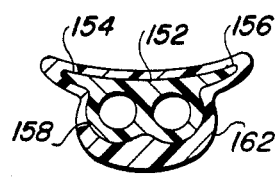
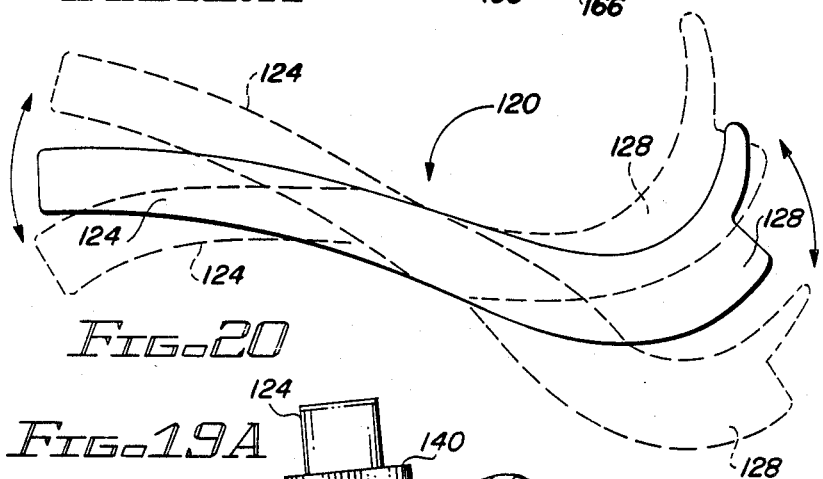
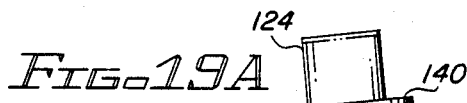
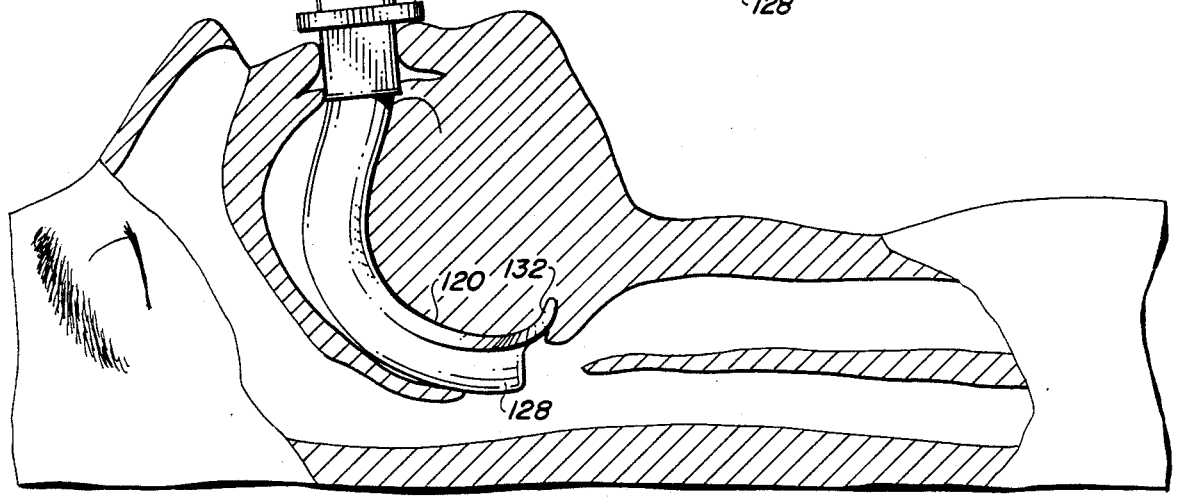
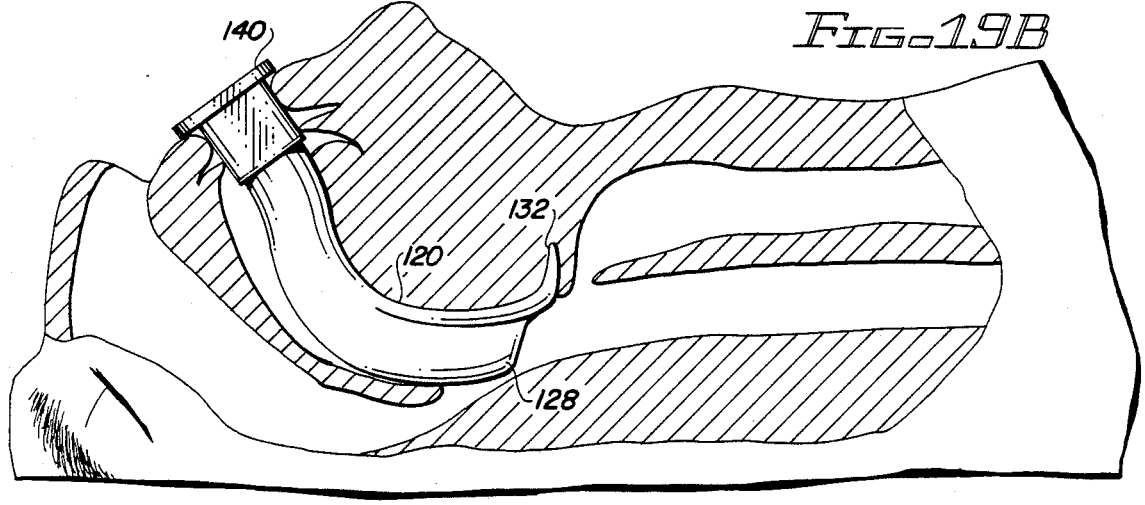

FLEXIBLE ORAL AIRWAYS AND METHODS

BACKGROUND OF THE INVENTION

1. Field of the Invention

The present invention relates generally to the medical arts, and particularly to a class of medical devices commonly referred to as oral airways which are inserted into the pharynx of a patient through the mouth while the patient is under anesthesia or is undertaking respiratory treatment.

2. Description of the Prior Art

While a surgery patient is under a general anesthesia, it is absolutely essential to maintain an unobstructed airway for the patient. Present commercially available oral airways are relatively rigid, and require about 15 different sizes to fit the variety of airway sizes that the anesthesiologist encounters. These multiple sizes often make it difficult to find an airway size that best fits the patient's particular airway dimensions. Further, it is a frequent occurrence after insertion of present commercially available airways that hypoxia is encountered after induction.

Gereg, in U.S. Pat. No. 4,498,473, discloses an inflatable tracheal tube which is rendered relatively stiff during insertion, and which thereafter may have a portion of the inflating fluid withdrawn to render the tube more flexible when in place. In U.S. Pat. No. 2,599,521, Berman discloses an H-shaped oral airway fabricated from a relatively soft elastomer so as to avoid the patient trauma caused by the hard rubber or metal oral airways that were in use prior to his development. A similar disclosure is made by Elmore in U.S. Pat. No. 2,705,959, wherein the material from which an oral airway is fabricated is semi-flexible. In U.S. Pat. No. 3,419,004, Berman also discloses an oral airway fabricated from a soft elastomer into a generally X configuration, and with a telescoping bite block.

In U.S. Pat. No. 3,930,507, Berman discloses an adjustable oral airway having a superior section and an inferior section joined by a hinge, and slideably secured together at the mouthpiece end by a tongue and groove slideable joint. The space between the two sections may then be adjusted by sliding the upper and lower sections of the mouthpiece, in order to expand or reduce the pharynx or lift the epiglottis.

Other prior art of interest includes the following U.S. Pat. Nos.: 2,099,127 to Leech; 3,306,298 to Raimo; 3,576,187 to Oddera; 3,756,244 to Kinnear et al; 3,908,665 to Moses; 3,926,196 to Bornhorst et al; 4,033,353 to LaRosa; 4,054,135 to Berman; 4,112,936 to Blachly; 4,148,308 to Sayer; 4,198,970 to Luomanen; and 4,270,531 to Blachly.

SUMMARY OF THE INVENTION

The present invention has as its principal purpose the provision of an artificial airway dimensioned to extend through the oral airway of a medical patient during treatment, the artificial airway having a longitudinal air passageway and being sufficiently pliable so as to conform to the specific configuration of the particular patient during insertion but having means rendering the oral airway sufficiently rigid so as to maintain the specific patient configuration during insertion and avoid bending in certain directions. To this end, means are provided for rendering the oral airway relatively flexible at all times without manipulation in a direction which is generally transverse to the curvature of a patient's oral passageway, and relatively rigid laterally and generally in the direction of the plane of the oral airway as it extends through the patient's pharynx, the oral airway being further provided with sufficient stiffness in the longitudinal direction so as to permit extension through the patient's oral pharynx.

To achieve the purposes described above, the oral airway comprises an airway member having dimensions which generally conform to the dimensions of human airways, the airway member being formed of a plastic material which is easily molded to the configuration of the specific patient airway during insertion with an air passageway extending longitudinally through the airway member. The airway member is provided with a spine extending longitudinally through the airway member and generally parallel with at least a portion of the air passageway, the spine being formed of a material which is relatively rigid with respect to the plastic material of the airway member, and with the spine being sufficiently flexible to conform with the airway member to the dimensions of the specific patient airway during insertion, but sufficiently rigid to maintain that configuration after insertion.

In a preferred embodiment of the present invention, the airway member comprises a proximal portion and a distal portion, the proximal portion being relatively straight and with the distal portion extending continuously from the proximal portion and having a curve defined by inner and outer curved surfaces, and with the curve generally conforming to the dimensions of a human oral pharynx. To obtain the desired flexibility-rigidity characteristics of the airway as discussed above, it is preferred that the spine be formed of a ribbon spine having a relatively wide dimension in a plane generally parallel with the inner curved surface and extending internally through the airway member between the air passageway and that inner curved surface and being relatively thin so as to achieve the desired rigidity characteristic. The internal rigid ribbon along the distal portion is surrounded by the flexible material. Thus, the entire airway member is rendered relatively flexible in response to bending in directions normal to the curved surfaces and relatively inflexible to bending in directions parallel to those surfaces.

Other features may be employed in the preferred embodiment of the oral airway of the present invention to enhance the flexibility-rigidity characteristics discussed above. For example, in one embodiment it is preferred that plural ribs of the relatively rigid material be provided and extend from the ribbon spine into the airway member toward the outer surface. Suitably, the ribs are positioned outside of the air passageway. In another embodiment, the ribs may surround the air passageway.

Further, the oral airway may be provided with wings extending from the airway member along the distal portion and generally in the plane of the inner curved surface to enhance the rigidity characteristics of the airway member in the lateral direction. It is also suitable that the rigid ribbon spine extend outwardly into these wings.

The airway member may further be provided with an extending tongue at the distal extremity to serve as an epiglottis elevator, and with the flat ribbon spine extending through the epiglottis elevator to impart a desired degree of rigidity along that portion as well.

In order to impart the desired degree of flexibility to the airway member and the desired degree of rigidity to the spine, it has been found suitable to use non-toxic, polyresinous materials having a durometer rating on the order of between about ten to forty for the flexible material and on the order of between about forty and seventy for the spine and ribs (where ribs are included).

DESCRIPTION OF THE DRAWINGS

FIG. 4 is a cross-sectional side view of an oral airway construction in accordance with one embodiment of the present invention.

FIGS. 5(A) through 5(E) are cross-sectional elevations of the oral airway shown in FIG. 4, taken along respective sections thereof.

FIG. 6 is a perspective view of one embodiment of a bite block in accordance with the present invention.

FIG. 7 is a perspective view illustrating another embodiment of an oral airway in accordance with the present invention.

FIGS. 8(A) and 8(B) illustrate cross-sectional side and top plan views respectively, of the oral airway embodiment shown in FIG. 7.

FIGS. 9(A) through 9(E) illustrate cross-sectional elevations of the oral airway shown in FIGS. 8(A) and 8(B).

FIG. 10 is a cross-sectional side view of a third embodiment of an oral airway in accordance with the present invention.

FIG. 11 is a cross-sectional side view of a fourth embodiment of an oral airway in accordance with the present invention.

FIG. 12(A) is top plan view of the embodiment of FIG. 11, and FIG. 12(B) is a cross-sectional view taken along the mid-section of the embodiment of FIG. 11.

FIG. 13 is a perspective view of the rib structure of the airway shown in FIG. 11.

FIGS. 14(A) and 14(B) are cross-sectional side and top views, respectively, of another embodiment of the present invention, interior features shown by dotted lines.

FIGS. 15(A) through 15(D) are cross-sectional elevations of the oral airway shown in FIG. 14(b), taken along the respective cross-sectional lines.

FIGS. 16(A) and 16(B) are side views and and FIG. 16(C) is a perspective view, all illustrating a second embodiment of an adjustable bite block in accordance with the present invention.

FIGS. 17(A) and (B) are side and top views, respectively, of another embodiment of an oral airway according to this invention.

FIGS. 19(A) and 19(B) are cross-sectional views illustrating the use of oral airways in accordance with the present invention.

FIG. 20 is a side view illustrating the flexible characteristics of adjustable oral airways in accordance with the present invention.

FIG. 18(A) through (D) are cross-sectioned views of the oral airway shown in FIGS. 17(A) and (B), taken along respective cross-sectional lines.

DETAILED DESCRIPTION

Figure 1:
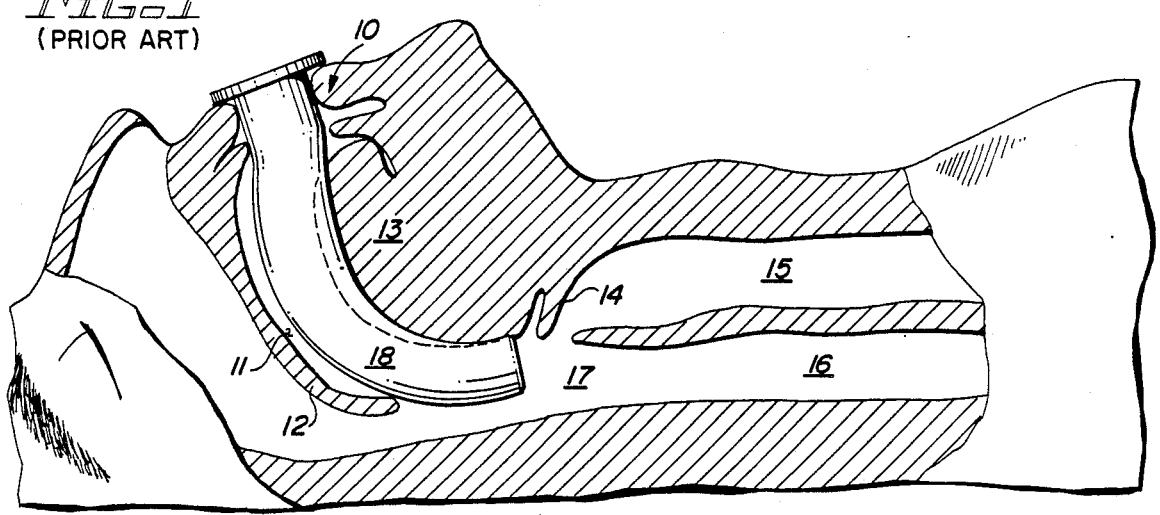
FIGS. 1, 2 and 3 are cross-sectional side views illustrating the use of prior art artificial airways inserted in a patient's pharynx.

Some of the difficulties associated with the use of prior art artificial oral airways will now be described with reference to FIGS. 1, 2 and 3. Noting FIG. 1, there is shown a simplified anatomical illustration of a patient's head, including the oral airway defined by the mouth 10, the oral cavity 11, the tongue 13, the epiglottis 14, the trachea 15, the esophogus 16 and pharynx 17. Fitted within the patient's oral airway is an artificial airway 18 which is demonstrated in FIG. 1 as representing a relatively good fit. It will be understood that conventional artificial airways, such as that shown as element 18 in FIG. 1, are generally fabricated from semi-flexible materials, such as a number of polyresins. However, it has heretofore been the manufacturing practice for such artificial oral airways to render such plastic materials relatively stiff to insure that the artificial airway can be inserted through the patient's oral airway.

Figure 2:
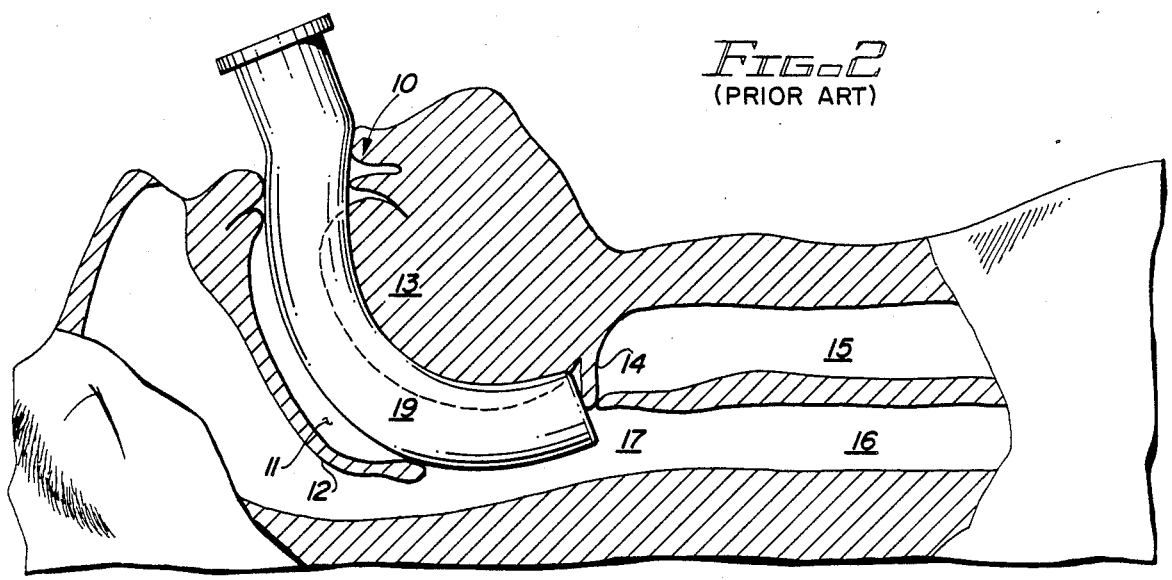
Figure 3:
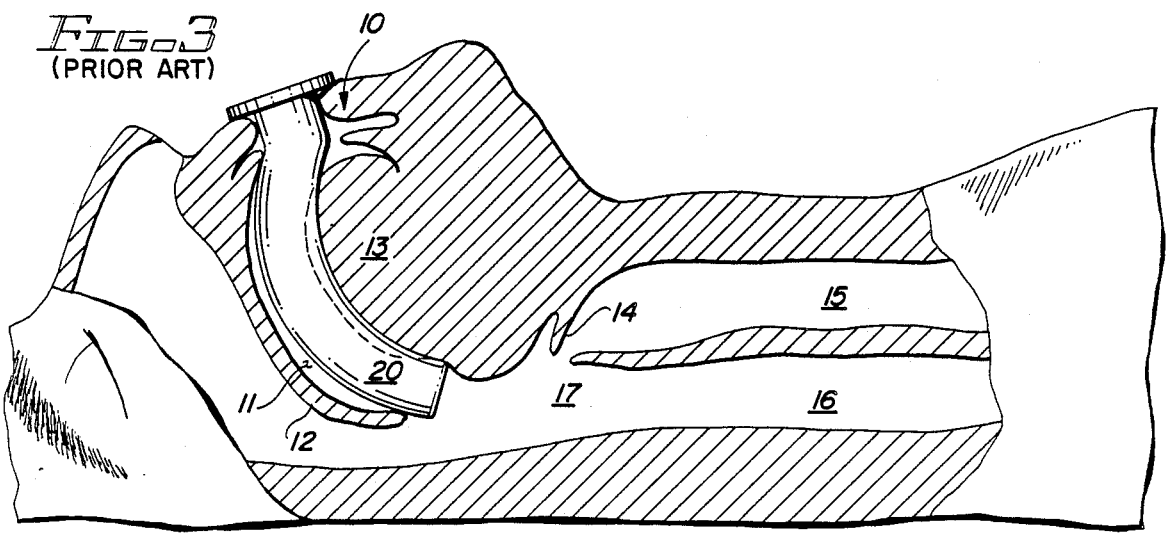

FIG. 2 illustrates a view similar to that of FIG. 1, in which the same reference numerals refer to the same anatomical features of the patient. Artificial airway 19 is depicted as being oversized with respect to the specific dimensions of the patient's oral airway, and thus represents a poor fit which often results in the epiglottis being forced into and over the tracheal opening, closing the airway at the tracheal opening. Likewise, FIG. 3 illustrates a poor fit, in the sense that the oral airway 20 is undersized with respect to the dimensions of the patient's oral airway such that the patient's tongue obstructs the artificial airway; also, the posterior tongue is frequently forced against the epiglottis, forcing it against the tracheal opening and causing an obstruction of the airway at the trachea.

A first embodiment of an oral airway in accordance with the present invention is shown in FIGS. 4, 5(a) through 5(e) and FIG. 6. This first embodiment of an oral airway in accordance with the present invention is referred to generally by the reference numeral 30, and comprises an airway member 22 having dimensions generally conforming to the dimensions of human airways, but being of a relatively uniform dimension. In this regard, it is presently the practice to have fifteen or more different sizes of artificial airways to accommodate the different sizes of human oral airways with which the anesthesiologist generally comes in contact. With respect to the present invention, it is contemplated that there will only be four, and at most six, different sizes in the general range of small, medium and large. Thus, the term "generally conforming to the dimensions of human airways" is simply intended to mean that the dimensions of the airway member 22 are such that the dimensions reasonably approximate that of human airways, but such dimensions are not critical for purposes of the present invention; indeed, it is a primary purpose of the present invention to avoid the requirement for the inventorying of a wide variety of oral airways of different dimensional characteristics.

Turning again to FIGS. 4, 5(a)-5(e) and 6, the airway member 22 is formed from a plastic or pliable material which is easily molded to the configuration of the specific patient airway during insertion. Suitable materials include a number of known flexible polyresins. In accordance with the present invention, it is preferred that the flexible material forming the airway member 22 has a durometer rating on the order of between about ten to forty.

The airway member 22 includes a longitudinal air passageway 23 extending completely through the airway member 22. The airway member 22 comprises a proximal portion 24 terminating at the proximal end 26, and a distal portion 28 which terminates at the distal end 30 and along the upper portion at an epiglottis elevator 32.

The airway member 22 is provided with a spine 34 which extends longitudinally through the airway member and generally parallel with at least a portion of the air passageway 23. The spine 34 is formed of a material which is relatively rigid with respect to the pliable material of the airway member 22, with the spine 34 being sufficiently flexible to conform with the airway member 22 to a specific patient airway during insertion, but being sufficiently rigid to maintain the patient's particular configuration after insertion. To achieve these goals, it is preferred to use for the spine a relatively rigid plastic material (which again may comprise known polyresins) having a durometer rating on the order of between about forty to seventy. It will of course be understood by those skilled in the art that the spine 34 may likewise be formed of other materials, such as known non-toxic metals.

As is shown in FIG. 4, the distal portion 28 of the airway member 22 is curved generally in the configuration of a normal human oral pharynx, and which curve is defined by an inner curved surface 29 and an outer curved surface 31. The spine 34 principally comprises a generally flat ribbon having a relatively wide dimension in a plane generally parallel with the inner curved surface 29 and which has a relatively thin dimension normal to the inner curved surface, whereby the distal portion 28 of the airway member is rendered relatively flexible in response to bending in directions normal to the surfaces 29 and 31, and relatively inflexible to bending in directions parallel to those surfaces. This feature is seen in comparing the side view of the upper flat ribbon portion of the spine 34 in FIGS. 4 and 5(a) through 5(e).

As will be described in greater detail below with reference to other drawing figures which illustrate different embodiments of the present invention, the flat ribbon spine may be used alone to achieve the desired flexibility-rigidity characteristics necessary to achieve the objects of this invention. However, the embodiment of the oral airway 30 shown in FIGS. 4 and 5(a) through 5(e) also utilizes plural ribs 36 which extend laterally from the flat ribbon spine 34, downwardly toward the outer curved surface 31 and (in the embodiment of FIG. 4) form a closed loop around the air passageway 23. This feature is particularly shown in the illustrations of FIGS. 5(a) through 5(d). As is shown in FIG. 5(e), the flat ribbon spine 34 may extend to the distal extremity of the epiglottis elevator 32. Further, as is shown in the left-hand portion of FIG. 4, the spine 34 likewise extends into the proximal portion 24 and to the proximal end 26; in the particular embodiment shown in FIG. 4, the flat ribbon spine 34 is shown to be interrupted along the proximal portion 24, and to contain closed loop ribs 36 which are bridged to the closed loop ribs in the distal portion 28 via a bridge 38.

Referring now to FIGS. 4 and 6, there is shown an adjustable bite block 40 having guard members 42 and a clip 44 along the longitudinal side thereof, which permits the bite block 40 to be adjustably moved along the proximal portion 24 of the airway member 22 to a specific desired position after the oral airway 30 has been inserted into the patient's airway. Once positioned at the desired location, the clip 44 may then be connected together to lock the bite block 40 in place.

A second embodiment of a flexible oral airway in accordance with the present invention will now be described with reference to FIGS. 7, 8(a), 8(b) and FIGS. 9(a) through 9(f). This second embodiment of an oral airway is referred to generally by the reference numeral 50, and includes an airway member 52 with proximal and distal portions thereof designated by the reference numerals 54 and 56, respectively. The airway member 52 includes air passageway means which, in this example, comprises three independent air passageways 53, which extend parallel with each other and longitudinally through the airway member 52 from the end of the proximal portion 54 to the end of the distal portion 56. The provision of such multiple independent passageways permits multiple uses to be made of the oral airway 50. For example, one of the independent passageways 53 may be utilized for administering medication, for a suction tube or for other, similar uses.

The airway member 52 is fabricated from a pliable plastic material, such as that described above with reference to the airway member 22 of FIG. 4. Likewise, the airway member 52 is provided with a relatively rigid spine formed of a generally flat ribbon 64 which extends from the extremity of the proximal portion 54, continuously through the distal portion 56 and into the epiglottis elevator 62. As is shown in FIG. 8(a), the flat ribbon spine 64 is positioned between the air passageways 53 and the inner curved surface 59; and as is shown in FIGS. 8(b) and 9(a) through 9(f), is generally parallel to the plane of the inner curved surface 59. Additionally, the oral airway 50 is provided with plural wings 66 and 68 which flare outwardly from near the interface of the proximal and distal portions 54, 56 and then taper inwardly near the distal extremity of the distal portion 56, and at the base of the epiglottis elevator 62. As is shown in FIGS. 9(b)–9(f), the flared portion forming the wings 66 and 68 may be flared upwardly as the dimensions of the wings 66, 68 extend outwardly away from the flat ribbon spine 64 to thus conform to the general contours of the patient's oral airway during insertion.

It will be understood that the adjustable bite block discussed above with reference to FIGS. 4 and 6 and the adjustable bite block discussed below with reference to FIGS. 16(a)–(c) may be utilized with the oral airway 50 just described.

Variations of the oral airway 50 will now be described with reference to FIGS. 10 and 11. In FIG. 10, an oral airway 70 is shown which includes an airway member 72, an air passageway 74 and a spine 76 formed of a ribbon of a hard plastic material imparting the desired rigidity, and which lies in the outside extremity of the air passageway 74. In the embodiment of FIG. 11, an oral airway 80 includes an airway member 82 having a longitudinal air passageway 84 and a spine 86 which extends from the epiglottis elevator 88 and only partially through the distal portion of the airway member 82. Reference is now made to FIGS. 12(a) and 12(b), which illustrate the top plan and cross-sectional views of typical oral airway constructions according to this invention, and which specifically denote the embodiments shown in FIGS. 10 and 11. In FIGS. 12(a) and 12(b), the reference numeral 90 refers generally to the oral airway having air passageways 92, flared wings 94 and 96 and an inner curved surface 98.

Attention is now drawn to FIGS. 13, 14(a), 14(b) and 15(a)–15(d) which illustrate another embodiment of an oral airway of this invention. With specific reference to FIG. 13, the oral airway is referred to generally by the reference numeral 120 and includes an airway member 122 defined by a proximal portion 124 and a distal portion 128. Multiple longitudinal air passageways 123 extend from the proximal end 126 to the lower extremity of the distal portion 128. The oral airway 120 further includes an epiglottis elevator 132 which functions in a manner similar to the epiglottis elevator as discussed above with reference to the embodiments shown in FIGS. 4 and 7. The oral airway 120 is further defined by inner and out curved surfaces 129 and 131, as shown in FIG. 14(a).

The oral airway 120 is provided with a spine 134 that extends generally parallel with the air passageways 123 and generally parallel to the plane of the inner curved surface 129. As is depicted in FIG. 14(a), the spine 134 extends to the distal extremity of the epiglottis elevator 132.

In the arrangement of the oral airway 120 shown in FIGS. 14(a) and 14(b), and as specifically illustrated in FIGS. 15(a) through 15(d), plural independent ribs 138 are provided extending laterally from the flat ribbon spine 134 and toward the outer curved surface 131. In contrast to the ribs 36 shown in FIG. 4, the ribs 138 in this embodiment do not form a closed loop about the air passageways 123. The ribs 138 may be formed of a relatively rigid plastic material and molded integrally with the flat ribbon spine 134.

The oral airway 120 further includes a pair of flared wings 166, 168 along the distal portion of the airway member 122. In this arrangement, the flat ribbon spine 134 extends laterally outwardly on the sides thereof and into the molded plastic material forming the wings 166 and 168, in the distal portion 128 of the airway member 122 (see FIGS. 15(a)–(c)).

An alternate form of an adjustable bite block will now be described with reference to FIGS. 16(a)–(c), in which reference numeral 140 generally refers generally to a tubular bite block conforming to the cross-sectional configuration of the proximal portion 124 of the airway member 122 (FIG. 13). The body 144 of the bite block 140 has a central passageway 145 dimensioned so as to pass over the proximal portion of any of the oral airways 20, 50, 70, 80, 90 or 120, all described above. The bite block 140 further includes laterally extending guards 142 formed of a generally flexible material which extend away from the body portion 144. The bite block 140 also includes a hinged member 143 rotatably coupled in the plane of the body portion 144 along the opening 145 with a friction surface 146 on the inside thereof. In use, the squeezing of the extensions 142, as shown in FIGS. 16(b) and (c), causes the hinged member 143 to rotate outwardly. The bite block 140 may then be pushed along the proximal portion of one of the oral airway members described above. When positioned at the desired location, the guards 142 are then released, permitting the hinged member 143 to return to the position shown in FIG. 16(a), thus causing the friction surface 146 to engage the outer surface of the airway member 122 and hold the bite block 140 in the desired position.

Another embodiment of the oral airway incorporating the features of this invention is shown in FIGS. 17(a) and (b) and FIGS. 18(a) through 18(d). This additional embodiment of the oral airway is referred to generally by the reference numeral 150 and FIGS. 17(a) and 17(b), and includes a relatively rigid spine 152 extending from the proximal end to the distal end above the multiple air passageways 160. The spine includes wings 154 and 156 along the distal portion of the oral airway 150. The spine further includes a distending rib portion 158 which surrounds the multiple air passageways 160, as is shown in FIGS. 18(a) through 18(d). The oral airway 150 further includes a body portion surrounding the spine 152, wings 154 and 156 and the distending rib portion 158. As described above, the body portion 162 is fabricated from a relatively flexible polyresin material, with respect to the relatively rigid material of the spine and its various portions. The oral airway 150 is further defined at the distal portion by inner and outer curved surfaces 164 and 166, and an epiglottis elevator 168.

FIGS. 19(a) and 19(b) illustrate the flexible characteristics of the oral airways of this invention. In FIG. 19(a), the oral airway 120 is shown extending into the patient's oral pharynx, and with the bite block 140 positioned at a desired location. It will be noted that a part of the proximal portion 124 extends outwardly from the patient's mouth. As can be seen, the epiglottis elevator 132 extends upward and under the epiglottis to avoid obstructions in the esophagus.

FIG. 19(b) shows the flexible characteristics of the oral airway 120 when the patient's neck is extended. Again, it will be noted that the epiglottis elevator 132 extends upwardly and maintains the epiglottis away from the esophagus. With respect to the positioning of the oral airway 120 in FIG. 19(a), it will be noted that the oral airway is capable of a substantial amount of downward bending without adversely affecting the position of the oral airway with respect to the epiglottis and the esophagus.

The general bending characteristics of an oral airway, such as oral airway 120, in accordance with the present invention is shown in FIG. 20, where reference numerals 124 and 128 again refer to the proximal and distal portions, respectively, of the oral airway 120 shown in FIG. 13. It will be noted that the proximal portion 124 is capable of a substantial amount of bending about the approximate joinder point with the distal portion 128, in both upward and downward directions. It will also be noted that the distal portion 128 is capable of a substantial amount of flexibility in the vertical direction. However, it will be appreciated by those skilled in the art that the flat ribbon spine (such as element 134 in FIGS. 14(a) and 14(b)) precludes lateral bending which may otherwise cause patient trauma.

I claim:

1. An oral airway comprising:
    an airway member having dimensions generally conforming to the dimensions of human airways, said airway member formed from a plastic material which is easily molded to the configuration of a specific patient airway during insertion, said member having an air passageway extending longitudinally therethrough; and
    a spine extending longitudinally through and fixed with said airway member and generally parallel with at least a portion of said air passageway, said spine formed of a material which is rigid relative to the plastic material of said airway member, said spine being sufficiently flexible to conform with said airway member to said specific patient airway during insertion, and sufficiently rigid to maintain said configuration after insertion.

2. The oral airway recited in claim 1 wherein said spine is flexible laterally with respect to the longitudinal direction of said air passageway.

3. The oral airway recited in claim 1 wherein said airway member comprise a proximal portion and a distal portion, said proximal portion being relatively straight, said distal portion extending continuously from said proximal portion and having a curve defined by inner and outer curved surfaces.

4. The oral airway recited in claim 3 wherein said spine comprises a distal section extending through said distal portion of said airway member and adjacent said inner curved surface.

5. The oral airway recited in claim 4 further comprising rib means extending laterally from said spine distal section and alongside said passageway.

6. The oral airway recited in claim 5 wherein said rib means comprises plural ribs spaced apart along said distal portion of said airway member.

7. The oral airway recited in claim 6 wherein some of said plural ribs form a closed loop laterally through said distal portion of said airway member and around said passageway.

8. The oral airway recited in claim 4 further comprising a proximal spine section formed of rib means extending along said proximal portion of said airway member.

9. The oral airway recited in claim 8 wherein said rib means along said proximal spine section forms a closed loop laterally through said proximal portion of said airway member and around said passageway.

10. The oral airway recited in claim 9 wherein said rib means forms plural ribs, each rib connected to adjacent ribs alternately at one side and then the other side in the longitudinal direction along said proximal portion of said airway member.

11. The oral airway recited in claim 4 wherein said spine comprises a generally flat ribbon having a relatively wide dimension in a plane generally parallel with said inner curved surface and a relatively thin dimension normal to said inner curve surface, whereby said distal portion of said airway member is rendered relatively flexible in response to bending in directions normal to said inner surface and relatively inflexible to bending in directions parallel to said inner surface.

12. The oral airway recited in claim 11 wherein said airway member further includes an extending tongue along said inner surface at the distal extremity of said distal portion, said flat ribbon spine extending through said tongue and wherein said extending tongue functions as an epiglottis elevator when said oral airway is properly inserted in a patient's oral airway.

13. The oral airway recited in claim 11 wherein said flat ribbon spine extends continuously through said proximal and distal portions of said airway member.

14. The oral airway recited in claim 13 wherein said airway member includes molded wings extending outwardly from the sides thereof and generally parallel to the plane of said inner surface.

15. The oral airway recited in claim 14 wherein said wings flare outwardly from near the interface of said proximal and distal portions and then taper inwardly near the distal extremity of said distal portion.

16. The oral airway recited in claim 15 wherein said flat ribbon of said spine extends into said wings.

17. The oral airway recited in claim 11 wherein said air passageway comprises multiple independent and parallel passageways extending centrally and longitudinally through said airway member.

18. The oral airway recited in claim 11 wherein said spine further comprises rib means extending from said flat ribbon and through said airway toward said inner curved surface, with said air passageway within said rib means.

19. The oral airway recited in claim 3 further comprising an adjustable bite block dimensioned to slide along said proximal portion, said bite block having means for engaging said proximal portion at any desired position.

20. The oral airway recited in claim 19 wherein said bite block includes an opening for extending said proximal portion of said airway member therethrough, said engaging means comprising a locking arm extending into said bite block opening.

21. The oral airway recited in claim 20 wherein said locking arm is engageable and disengageable with said proximal portion of said airway member responsive to finger pressure along the periphery of said bite block.

22. An oral airway comprising:
an airway member having
a proximal portion dimensioned to extend generally through the mouth of a patient,
a curved distal portion dimensioned to extend from said proximal portion through the oral pharynx of the patient and to an area near the patient's epiglottis, the curve of said distal portion defined by inner and outer curved surfaces with said inner curved surface being relatively flat and adapted to rest along the back of the patient's tongue after insertion,
an air passageway extending longitudinally through said proximal and distal portions and generally parallel with the patient's airway,
at least said distal portion of said airway member formed of a pliable material that is easily molded to the configuration of a particular patient's oral airway during insertion; and
means extending longitudinally along said distal portion of said airway member for rendering said distal portion relatively flexible to bending forces generally normal to said inner surface, and relatively inflexible to bending forces parallel to the flat plane of said inner surface.

23. The oral airway recited in claim 22 wherein said longitudinally extending means comprises a flat ribbon spine adjacent to, and extending generally parallel with said inner curved surface, said flat ribbon spine having a relatively wide dimension generally parallel with such inner curved surface and a relatively narrow dimension generally normal to said inner curved surface.

24. The oral airway recited in claim 23 further comprising rib means extending laterally from flat ribbon spine along said distal portion of said airway member and about said air passageway.

25. The oral airway recited in claim 24 wherein said rib means forms a closed loop laterally through said distal portion of said airway member and around said passageway.

26. The oral airway recited in claim 24 wherein said flat ribbon spine includes a proximal spine section formed of plural ribs extending along said proximal portion.

27. The oral airway recited in claim 26 wherein some of said plural ribs along said proximal portion are connected to adjacent ribs alternately at one side and then the other side in the longitudinal direction along said proximal portion.

28. The oral airway recited in claim 23 wherein said flat ribbon spine extends continuously through said proximal and distal portions of said airway member.

29. The oral airway recited in claim 23 wherein said airway member includes molded wings extending outwardly from the sides thereof and generally in the plane of said inner curved surface, and wherein said wings flare outwardly from near the interface of said proximal and distal portions and then taper inwardly near the distal extremity of said distal portion.

30. The oral airway recited in claim 22 further comprising an adjustable bite block dimensioned to slide along said proximal portion, said bite block having means for locking to said proximal portion at any desired position.

31. An oral airway comprising:
an airway member having
a proximal portion dimensioned to extend generally through the mouth of a patient;
curved distal portion dimensioned to extend from said proximal portion through the oral pharynx of the patient and to an area near the patient's epiglottis, the curve of said distal portion defined by inner and outer curved surfaces with said inner curved surface being relatively flat and adapted to rest along the back of the patient's tongue after insertion;
an air passageway extending longitudinally through said proximal and distal portions and generally parallel with the patient's airway;
at least said distal portion of said airway member formed of a pliable material that is easily molded to the configuration of a particular patient's oral airway during insertion;
a generally flat spine of a material which is inflexible to bending with respect to said airway member, said flat spine extending through said distal portion adjacent to and generally parallel with said inner curve surface; and
rib means of said inflexible material extending laterally from said spine and toward said outer surface, said rib means extending along said distal portion.

32. The oral airway recited in claim 31 wherein said airway member further includes an extending tongue along said inner curved surface at the distal extremity of said distal portion with said flat ribbon spine extending through said tongue, and wherein said tongue functions as an epiglottis elevator when said oral airway is properly inserted in a patient's oral airway.

33. The oral airway recited in claim 31 further comprising a proximal spine section formed of rib means extending along said proximal portion, said rib mean extending laterally through said proximal portion of said airway member and around said passageway.

34. The oral airway recited in claim 31 wherein said pliable material of said airway member has a durometer rating on the order of ten to forty.

35. The oral airway recited in claim 31 wherein said inflexible material of said spine has a durometer rating on the order of between forty to seventy.

36. An oral airway comprising:
an airway member having
a proximal portion dimensioned to extend generally through the mouth of a patient,
a curved distal portion dimensioned to extend from said proximal portion through the oral pharynx of the patient and to an area near the patient's epiglottis, the curve of said distal portion defined by inner and outer curved surfaces with said inner curved surface being relatively flat and adapted to rest along the back of the patient's tongue after insertion,
an air passageway extending longitudinally through said proximal and distal portions and generally parallel with the patient's airway,
at least said distal portion of said airway member formed of a pliable material that is easily molded to the configuration of a particular patient's oral airway during insertion;
a flat ribbon spine extending longitudinally along said distal portion of said airway member and generally parallel with the plane of said inner surface, said flat ribbon spine formed of a material which is relatively flexible to bending forces generally normal to said inner surface and relatively inflexible to bending forces parallel to the flat plane of said inner surface; and
an extending tongue along said inner surface at the distal extremity of said distal portion, said flat ribbon spine extending through said tongue whereby said tongue functions as an epiglottis elevator when said oral airway is inserted into a patient.

37. The oral airway recited in claim 36 wherein said flat ribbon spine extends continuously along said proximal portion of said airway member from said distal portion thereof.

38. The oral airway recited in claim 37 wherein said pliable material has a durometer rating of the order of between ten to forty, and said inflexible material of said spine has a durometer rating on the order of between forty to seventy, with the durometer rating of said inflexible material being substantially greater than the rating of said flexible material.

39. An oral airway comprising:
an airway member having dimensions generally conforming to the dimensions of human airways, said airway member formed from a pliable material having a durometer rating on the order of between ten to forty and which is easily molded to the configuration of the specific patient airway during insertion, said member having an air passageway extending longitudinally therethrough;
a spine extending longitudinally through said airway member and generally parallel with at least a portion of said air passageway, said spine formed of a material which has a durometer rating on the order of about forty to seventy and which is rigid relative to the material of said airway member, said spine being sufficiently flexible to conform with said airway member to said specific patient airway during insertion, and sufficiently rigid to maintain said configuration after insertion and during patient neck extension and distension.

40. The oral airway recited in claim 39 wherein said spine includes extending rib means about said air passageway.

41. The oral airway recited in claim 39 wherein said air passageway comprises multiple independent and parallel passageways extending centrally and longitudinally through said airway member and said rib means.

42. The oral airway recited in claim 39 wherein said airway member comprises a proximal portion and a distal portion, said proximal portion being relatively straight and said distal portion extending continuously from said proximal portion and having a curve defined by inner and outer curved surfaces, said airway member including molded wings extending outwardly from the sides thereof and generally parallel to the plane of said inner surface, and wherein said wings flare outwardly from near the interface of said proximal and distal portions and then taper inwardly near the distal extremity of said distal portion.

43. The oral airway recited in claim 42 wherein said airway member further included an extending tongue along said inner surface at the distal extremity of said distal portion said spine extending through said tongue and wherein said tongue functions as an epiglottis elevator when said oral airway is properly inserted in a patient's oral airway.

44. A method for fabricating an oral airway which is capable of conforming to the specific dimensions of a particular patient's mouth and throat during insertion of the oral airway, said method comprising the steps of:
  molding an airway member from a pliable material which is capable of deformation responsive to bending forces during insertion of said airway member through a patient's mouth and throat;
  forming an air passageway longitudinally through said airway member; and
  forming a spine longitudinally along said airway member, said spine comprising of a material which is relatively rigid with respect to the material of said airway member, and is sufficiently flexible to conform with said airway member to said specific patient airway during insertion but sufficiently rigid to maintain said configuration after insertion.

45. The method recited in claim 44 wherein said airway member has a durometer rating on the order of between about ten to forty, and said spine has a durometer rating on the order of between about forty to seventy, with the durometer rating of said spine being substantially greater than than of said airway member.

* * * * *